United States Patent [19]

Ziegler et al.

[11] Patent Number: 5,554,735
[45] Date of Patent: Sep. 10, 1996

[54] AZO OXIME ETHERS AND THEIR USE AS FUNGICIDES

[75] Inventors: Hugo Ziegler, Witterswil, Switzerland; Stephan Trah, Freiburg, Germany

[73] Assignee: Ciba-Geigy Corporation, Tarrytown, N.Y.

[21] Appl. No.: 295,775

[22] Filed: Aug. 26, 1994

[30] Foreign Application Priority Data

Feb. 28, 1992 [CH] Switzerland ............... 624/92-4

[51] Int. Cl.$^6$ ............ C07C 245/02; C07C 245/04; C07C 251/12; A01N 33/26
[52] U.S. Cl. .................................. 534/738; 534/728
[58] Field of Search .................... 534/738, 728; 514/150

[56] References Cited

U.S. PATENT DOCUMENTS 4,270,947  6/1981  Gutman ........................ 534/738 X

FOREIGN PATENT DOCUMENTS

| 0370629A1 | 5/1990 | European Pat. Off. ........ 534/738 |
| 0414299A1 | 2/1991 | European Pat. Off. ........ 534/738 |
| 0460575A1 | 12/1991 | European Pat. Off. ........ 564/245 |
| 42-3391 | 2/1967 | Japan ......................... 534/738 |
| WO9007493 | 7/1990 | WIPO .......................... 564/245 |

Primary Examiner—Floyd D. Higel
Attorney, Agent, or Firm—Edward McC. Roberts

[57] ABSTRACT

Azo oxime ethers of formula (I), in which X is CH or N, $R_1$ is hydrogen, $C_1$–$C_3$ alkyl, trifluoromethyl or cylclopopy and $R_2$ is aryl or heteroaryl, have an activity against phytopathogenic fungi. They can be used in the form of formulaions as crop protection products, seed-dressing products and wood preservatives.

22 Claims, No Drawings

AZO OXIME ETHERS AND THEIR USE AS FUNGICIDES

The present invention relates to novel azo oxime ethers, to processes for their preparation, to their use as fungicities as well as compositions which comprise the azo oxime ethers as active ingredients.

The azo oxime ethers according to the invention are those of the formula I

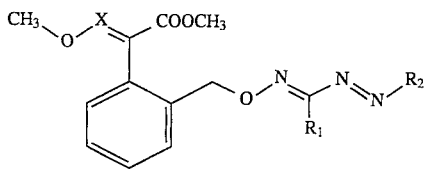

in which
X is CH or N,
$R_1$ is hydrogen, $C_1$–$C_3$alkyl, trifluoromethyl or cyclopropyl,
$R_2$ is aryl or heteroaryl, each of which is unsubstituted or substituted by one or more substituents R,
R is halogen; $C_1$–$C_6$alkyl; $C_3$–$C_6$cycloalkyl; $C_1$–$C_4$haloalkyl; $C_1$–$C_4$alkoxy; hydroxyl; phenyl, benzyloxy or aryloxy, each of which is unsubstituted or substituted by halogen, $C_1$–$C_4$alkyl, $C_1$–$C_6$alkoxy, trifluoromethyl or trifluoromethoxy; $C_1$–$C_4$haloalkoxy; cyano; nitro; mercapto; $C_1$–$C_4$alkylthio; $NR_3R_4$; $CONR_3R_4$; cyanomethyl; $SO_2NR_3R_4$; $COR_5$ or $COOR_5$,
$R_3$ and $R_4$ independently of one another are $C_1$–$C_4$alkyl or $R_3$ and $R_4$ together with the N atom form a 5–7-membered ring which can additionally contain 1–2 hetero atoms, and
$R_5$ is hydroxyl, $C_1$–$C_4$alkyl or aryl.

If there are asymmetric carbon atoms in the compounds of the formula I, the compounds are in optically active form. Due to the presence of the aliphatic, the azo and the imino double bond alone, the compounds are in any case in the [E] or [Z] form. Atropisomerism is also possible. The formula I is intended to embrace all these isomeric forms which are possible as well as mixtures thereof, for example racemic mixtures and any desired [E/Z] mixtures.

Aryl is to be understood as meaning, in particular, phenyl, naphthyl, tetrahydronaphthyl, fluorenyl or indanyl, heteroaryl is to be understood as meaning a heterocyclic group having aromatic character, such as pyridyl, pyrimidinyl, pyrazinyl, pyridazinyl, triazinyl, pyrazolyl, thiazolyl, thiadiazolyl, thienyl, isothiazolyl, isoxazolyl, tetrazolyl or triazolyl, or a group of this type to which benzene is fused, such as quinolinyl, isoquinolinyl, benzimidazolyl, benzothiazolyl, benzoxazolyl or phthalazinyl, or a group of this type to which a heterocycle is fused, such as purinyl, pteridinyl, pyrazolo[3,4-b]pyridyl or napthyridinyl. Heteroaryl is furthermore a phenyl group to which a heterocycle is fused, for example quinolinyl, isoquinolinyl, benzocoumarinyl, benzothiadiazolyl, carbazolyl, indolyl, indazolyl, benzothiazolyl, methylenedioxyphenyl or ethylenedioxyphenyl.

Alkyl groups in the above formula I and hereinafter are straight-chain or branched, depending on the number of the carbon atoms. $C_1$–$C_3$Alkyl is methyl, ethyl, propyl and isopropyl.

The aryl and heteroaryl groups can in each case have one or more substituents which are expediently one or more substituents selected from amongst halogen (in particular fluorine, chlorine and/or bromine), $C_1$–$C_6$alkyl (in particular methyl, ethyl, propyl, iso-propyl, butyl, iso-butyl and/or tert-butyl), $C_3$–$C_6$cycloalkyl (in particular cyclopropyl or cyclohexyl), $C_1$–$C_4$haloalkyl (in particular trifluoromethyl), $C_1$–$C_4$alkyloxy (in particular methoxy, ethoxy and/or butoxy), hydroxyl, benzyloxy which is unsubstituted or mono- or polysubstituted, aryloxy which is unsubstituted or mono- or polysubstituted, $C_1$–$C_4$haloalkoxy (in particular trifluoromethoxy), aryl, cyano, cyanomethyl, nitro, mercapto, $C_1$–$C_4$alkylthio, each of which is unsubstituted or mono- or polysubstituted (in particular methylmercapto and/or ethylmercapto), a group $NR_3R_4$, a group $CONR_3R_4$, a group $SO_2NR_3R_4$, a group $COR_5$ and a group $COOR_5$ (in which $R_3$ and $R_4$ are in each case $C_1$–$C_4$alkyl or $R_3$ and $R_4$ together form a 5–7-membered carbocyclic ring which can contain 1 to 2 hetero atoms (in particular morpholino), and $R_5$ is hydroxyl, $C_1$–$C_4$alkyl (in particular methyl or aryl).

Preferred substituents of the abovementioned benzyloxy, aryloxy and aryl groups are halogen (in particular fluorine, chlorine and bromine), $C_1$–$C_4$alkyl (in particular methyl), $C_1$–$C_4$alkoxy (in particular methoxy), trifluoromethyl and/or trifluoromethoxy.

The compounds according to the invention have fungicidal properties and are suitable as fungicidal active ingredients, in particular for use in agriculture and horticulture.

The invention furthermore relates to a process for the preparation of the compounds according to the invention, to fungicidal compositions comprising such compounds as active ingredients, and to the use of such compounds and compositions for controlling phytopathogenic fungi in agriculture and horticulture.

Important compounds of the formula I are those in which X, $R_1$ and R are as defined above and $R_2$ is phenyl, naphthyl, tetrahydronaphthyl, indanyl or fluorenyl, each of which is unsubstituted or substituted by one or more R, in particular those in which $R_2$ is phenyl which is unsubstituted or substituted by one or more R and in which R is fluorine, chlorine, bromine, $C_1$–$C_4$alkyl, cyclopropyl, cyclohexyl, trifluoromethyl, trifluoromethoxy, $C_1$–$C_4$alkoxy, morpholino, cyano, cyanomethyl, nitro, phenyl, phenoxy, hydroxyl, benzyloxy or $C_1$–$C_2$alkylthio.

Another group of important compounds of the formula I are those in which X, $R_1$ and R are as defined above and $R_2$, as heteroaryl, is a 5- or 6-membered heterocycle which has aromatic character and which is unsubstituted or substituted by one or more substituents R, in particular those compounds in which $R_2$ is pyridyl, pyrimidinyl, pyrazinyl, pyridazinyl or triazinyl, each of which is unsubstituted or substituted by one or more substituents R, or in which $R_2$ is pyrazolyl, thiazolyl, thiadiazolyl, thienyl, isothiazolyl, isoxazolyl, triazolyl or tetrazolyl, each of which is unsubstituted or substituted by one or more R.

Another group of important compounds of the formula I are those in which X, $R_1$ and R are as defined above and $R_2$ is a heterocycle which is unsubstituted or substituted by one or more R and to which benzene is fused, or is a phenyl group to which a heterocycle is fused, in particular in which $R_2$ is quinolinyl, isoquinolinyl, benzimidazolyl, benzothiazolyl, benzoxyazolyl, phthalazinyl, benzocoumarinyl, benzothiadiazolyl, carbazyl, indolyl or indazolyl, each of which is unsubstituted or substituted by one or more R.

Other important compounds of the formula I are those in which X, $R_1$ and R are as defined above and $R_2$ is methylenedioxyphenyl or ethylenedioxyphenyl, each of which is unsubstituted or substituted by one or more halogen, methyl or methoxy substituents, in particular those in which the methylene or ethylene bridge is substituted by fluorine.

Another group of important compounds of the formula I are those in which X, $R_1$ and R are as defined above and $R_2$ is a heterocycle which is unsubstituted or substituted by one or more R and to which a second heterocycle is fused, in particular those in which $R_2$ is purinyl, pteridinyl, pyrazolo[3,4-b]pyridyl or naphthyridinyl, each of which is unsubstituted or substituted by one or more R.

Another group of important compounds of the formula I are those in which X is CH and $R_2$ is phenyl which is monosubstituted to trisubstituted by identical or different substituents from the group comprising halogen, $C_1$–$C_2$alkyl, $C_1$–$C_2$alkoxy, CN and $CF_3$.

The process according to the invention for the preparation of the compounds according to the invention comprises reacting an azo oxime of the general formula $$R_2-N=N-C\begin{smallmatrix}R_1\\\\N-OH\end{smallmatrix} \quad II$$

in which $R_1$ and $R_2$ are as defined above, with a benzyl alcohol derivative of the general formula $$\text{III}$$

[structure: benzene ring with CH$_3$OX–C(=)–COOCH$_3$ and UCH$_2$– substituents]

in which U is a leaving group and X is CH or N.

This reaction is a nucleophilic substitution which can be carried out under the reaction conditions which are customary for such reactions. The leaving group U in the benzyl alcohol derivative of the formula III is preferably to be understood as meaning chlorine, bromine, iodine, mesyloxy or tosyloxy. The reaction is expediently carried out in an inert organic diluent such as a cyclic ether, for example tetrahydrofuran or dioxane, acetone, dimethylformamide or dimethyl sulfoxide, in the presence of a base such as sodium hydride, sodium carbonate or potassium carbonate, sodium amide, a tertiary amine, for example a trialkylamine, in particular diazabicyclononane or diazabicycloundecane, or silver oxide, at temperatures between –20° C. and 80° C., preferably in a temperature range from 0° C. to 20° C.

Alternatively, the reaction can be carried out at room temperature with phase transfer catalysis in an organic solvent, for example methylene chloride, in the presence of an aqueous basic solution, for example sodium hydroxide solution, and of a phase transfer catalyst, for example tetrabutylammonium hydrogen sulfate.

The resulting compounds of the formula I can be isolated and purified by methods known per se. Resulting isomer mixtures, for example E/Z isomer mixtures, can be separated into the pure isomers by methods known per se, for example by chromatography or fractional crystallisation.

The azo oximes of the formula II which are used in the processes according to the invention as starting materials are either known or can be prepared by methods known per se, as they are described in Houben-Weyl "Methoden der Organisthen Chemie" [Methods in Organic Chemistry], Volume 10/3, pages 622–624. (Azo oximes of the formula II are disclosed in EP-A-414 299 (SHELL).

The starting materials of the formula III can also be prepared in a manner known per se, for example as described in European Patent Publication EP-A-203 606 (BASF) and in the references cited therein, or as described in Angew. Chem. 71, 349–365 (1959).

The azo oximes of the formula II are preferably prepared by a) nitrosation of a hydrazone of the formula $$R_2-NHN=C\begin{smallmatrix}COOH\\\\R_1\end{smallmatrix} \quad IV$$

in which $R_1$ and $R_2$ are as defined above, with nitrous acid, in which process the azo oximes are obtained directly after decarboxylation and rearrangement. The reaction conditions can be found in Houben-Weyl "Methoden der organischen Chemie" [Methods in Organic Chemistry], Volume 10/3, pages 622–623.

The azo oximes of the formula II are furthermore preferably prepared by

B) dehydrogenating a hydrazine oxime of the formula $$R_2.NHNH-C\begin{smallmatrix}R_1\\\\N-OH\end{smallmatrix} \quad V$$

in which $R_1$ and $R_2$ are as defined above, with an oxidant such as iron(III) chloride or oxygen. The reaction conditions have been described by E. Bamberger and coworkers in Chem. Bet. 35, 54, 1084 (1902) and 36, 57 (1903).

A further process according to the invention for the preparation of the compounds of formula I comprises reacting a keto ester of the general formula VI (VI)

[structure: benzene ring with O=C–COOCH$_3$ group and CH$_2$–O–N=C(R$_1$)–N=N–R$_2$ chain]

in which $R_1$ and $R_2$ are as defined above, with a methhoxymethyltriphenylphosphonium salt of the formula VII or with O-methylhydroxylamin hydrohalide of the formula VIII, respectively, $$Ph-\overset{\oplus}{\underset{Ph}{\overset{Ph}{P}}}-CH_2-O-CH_3 \quad Z^{\ominus} \quad (VII)$$

$$CH_3-O-NH_2.H-Hal \quad (VIII)$$

in which Ph is phenyl and Z and Hal represent chloride, bromide or iodide.

The synthesis VI+VII represents a Witrig type reaction which can be carried out by known methods.

The synthesis VI+VIII is a condensation reaction which can be carried out under usual reaction conditions, e.g. described in EP-A-254 426, p. 19.

The compounds of the formula VI are obtained by reacting an azo oxime of the general formula II with a keto ester of the general formula IX (IX)

[structure: benzene ring with O=C–COOCH$_3$ group and CH$_2$–U substituent]

in which U is a leaving group as defined above.

The present invention refers also to the compounds of formula VI above.

A further process according to the invention for the preparation of the compounds of formula I wherein X is CH comprises reacting a phenyl acetate derivative of the general formula X

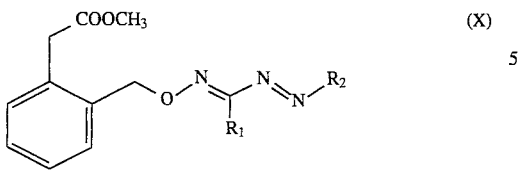

in which $R_1$ and $R_2$ are as defined above, with methylformate in a basic medium to obtain, as an intermediate product, the corresponding 3-hydroxy acrylic acid methylester which is then subjected to methylation. Agents that may be used for methylation are for example methyl iodide, dimethyl sulfate, diazomethan and the like. As bases there may be mentioned hydroxides, (hydrogen)carbonates and alcoholates of alkaline (Li, Na, K etc.) and alkaline earth (Ca, Mg etc.) metals, sodium hydride, tert.amines such as trimethylamine, triethylamine, pyridine, picolines, N-methylmorpholine, N-ethylpyrrolidine, diazabicyclo(4,3,O)-undecan (DBU), 1,4-diaza-bicyclo-2,2,2-octan (DABCO), diazabicyclo( 3,2,O)nonan (DBN) and the like.

The phenyl acetates of the formula X are obtained by reacting an azo oxime II with a phenyl acetate of the formula XI

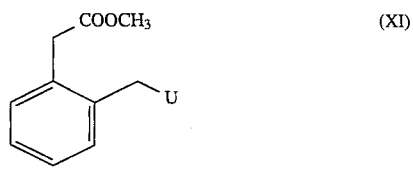

wherein U is a leaving group as defined above.

The present invention refers also to the compounds of formula X above.

The compounds of the formula I according to the invention have a fungicidal activity and can accordingly be used for controlling, or preventing, fungus infestation in agriculture, in horticulture and in the protection of wood. They are suitable, in particular, for inhibiting the growth, or for destroying, phytopathogenic fungi on parts of plants, for example leaves, stalks, roots, tubers, fruits or flowers, and on seed as well as soil-borne fungal pathogens. The compounds according to the invention can furthermore be used for controlling wood-destroying and wood-discolouring fungi. The compounds according to the invention are effective, for example, in the control of fungi from the classes of the Deutemmycetes, Ascomycetes, Basidiomycetes and Phycomycetes.

The compounds according to the invention are particularly suitable for controlling the following pathogens:

Powdery mildews (for example *Erysiphe graminis, Erysiphe cichomcearum, Podosphaera leucotricha, Uncinula necator*, Sphaerotheca spp.)

Rusts (for example *Puccinia tritici, Puccinia recondita, Puccinia hordei, Puccinia coronata, Puccinia strifformis, Puccinia arachidis, Hemileia vastatrix, Uromyces fabae*) scab fungi (for example *Venturia inaequalis*) Cercospora spp. (for example *Cercospora amchidicola, Cercospom bedcola*) Mycosphaerella spp. (for example *Mycosphaerella fijiensis*) Altemaria spp. (for example *Altemaria brassicae, Altemaria mali*) Septoria spp. (for example *Septoria nodorum*) Helminthosporium spp. (for example *Helminthosporium teres, Helminthosporium oryzea*) Plasmopara spp. (for example *Plasmopara viticola*) Pseudoperonospora spp. (for example *Pseudoperonospora cubensis*) Phytophthora spp. (for example *Phytophthora infestans*) Pseudocercosporella spp. (for example *Pseudocercosporella herpotrichoides*) Piricularia spp. (for example *Piricularia oryzae*)

Furthermore, the compounds have an activity against, for example, fungi from the genus Tilletia, Ustilago, Rhizoctonia, Verticillium, Fusarium, Pythium, Gaeumannomyces, Sclerotinia, Monilia, Botrytis, Peronospora, Bremia, Gloeosporium, Cercoporidium, Penicillium, Ceratocystis, Rhynchosporium, Pyrenophora, Diaporthe, Ramularia and Leptosphaeria. Moreover, some representatives of the compounds according to the invention also exhibit an activity against wood-damaging fungi, for example those from the genus Coniophora, Gloeophyllum, Poria, Merulius, Trametes, Aureobasidium, Sclerophoma and Trichoderma.

The compounds according to the invention are distinguished by a prophylactic and curative, but in particular by a pronounced systemic, activity.

Under greenhouse conditions, the compounds according to the invention have an activity against phytopathogenic fungi which starts at concentrations of 0.5 mg to 500 mg of active ingredient per litre of spray mixture. In the field, dosage rates of 20 g to 2 kg of active ingredient of the formula I are advantageously applied per hectare and treatment. To control seed- or soil-borne fungi by the seed-dressing method, it is advantageous to use dosage rates of 0.001 g to 1.0 g of active ingredient of the formula I per kg of seed.

The compounds according to the invention can be formulated to give a range of compositions, for example solutions, suspensions, emulsions, emulsifiable concentrates and preparations in the form of powders. The fungicidal compositions according to the invention comprise an effective amount of at least one compound of the general formula I as defined above, as well as formulation auxiliaries. The compositions expediently comprise at least one of the following formulation auxiliaries:

Solid carders; solvents or dispersants; surfactants (wetting agents and emulsifiers); dispersants (without surfactant action); and stabilisers.

The following are essentially suitable as solid carriers: natural mineral substances, such as kaolin, clays, kieselguhr, talc, bentonite, chalk, for example prepared chalk, magnesium carbonate, lime, quartz, dolomite, attapulgite, montmorillonite and diatomaceous earth; synthetic mineral substances, such as highly-disperse silica, alumina and silicates; organic substances such as cellulose, starch, ureas and synthetic resins; and fertilisers, such as phosphates and nitrates, it being possible for such carriers to exist, for example, in the form of granules or powders.

The following are essentially suitable as solvents or dispersants: aromatics, such as toluene, xylenes, benzene and alkylnaphthalenes; chlorinated aromatics and chlorinated aliphatic hydrocarbons such as chlorobenzenes, chloroethylenes and methylene chloride; aliphatic hydrocarbons such as cyclohexane and paraffins, for example mineral oil fractions; alcohols, such as butanol and glycol, as well as their ethers and esters; ketones, such as acetone, methyl ethyl ketone, methyl isobutyl ketone and cyclohexanone; and strongly polar solvents or dispersants, such as dimethylformamide, N-methylpyrrolidone and dimethyl sulfoxide, such solvents and dispersants preferably having flash points of at least 30° C. and boiling points of at least 50° C., and water. Other suitable substances in the group of the solvents or dispersants are so-called liquified gaseous extenders or carriers, which are products which are gaseous at room temperature and under atmospheric pressure. Examples of such products are, in particular, aerosol propellants. If water is used as a solvent, it is also possible to use, for example, organic solvents as auxiliary solvents.

The surfactants (wetting agents and emulsifiers) can be non-ionic compounds, such as condensation products of fatty acids, fatty alcohols or fatty-radical-substituted phenols with ethylene oxide; fatty acid esters and fatty acid ethers of sugars or polyhydric alcohols; the products which are obtained from sugars or polyhydric alcohols by condensation with ethylene oxide; block copolymers of ethylene oxide and propylene oxide; or alkyldimethylamine oxides.

The surfactants can also be anionic compounds such as soaps; fatty sulfate esters, for example sodium dodecyl sulfate, sodium octadecyl sulfate and sodium cetyl sulfate; alkylsulfonates, arylsulfonates and fatty aromatic sulfonates, such as alkylbenzenesulfonates, for example calcium dodecylbenzenesulfonate, and butylnaphthalenesulfonates; and more complex fatty sulfonates, for example the amide condensation products of oleic acid and N-methyltaurine, and the sodium sulfonate of dioctyl succinate.

Finally, the surfactants can be cationic compounds, such as alkyldimethylbenzylammonium chlorides, dialkyldimethylammonium chlorides, alkyltrimethylammonium chlorides and ethoxylated quaternary ammonium chlorides.

The following are essentially suitable as dispersants (without surfactant action): lignin, sodium salts and ammonium salts of ligninsulfonic acid, sodium salts of maleic anhydride/diisobutylene copolymers, sodium salts and ammonium salts of sulfonated polycondensation products of naphthalene and formaldehyde, and sulfite waste liquors.

Examples of dispersants which are particularly suitable as thickeners or anti-setting agents are, for example, methylcellulose, carboxymethylcellulose, hydroxyethylcellulose, polyvinyl alcohol, alginates, caseinates and blood albumin.

Examples of suitable stabilisers are acid-forming agents, for example epichlorohydrin, phenyl glycidyl ether, and soya epoxides; antioxidants, for example gallic esters and butylhydroxytoluene; UV absorbers, for example substituted benzophenones, diphenylacrylonitrilic esters and cinnamic esters; and deactivators, for example salts of ethylenediaminetetraacetic acid, and polyglycols.

Besides the active ingredients of the formula I, the fungicidal compositions according to the invention can also comprise other active ingredients, for example other fungicides, insecticides and acaricides, bactericides, plant growth regulators and fertilisers. Such combinations are suitable for broadening the spectrum of action or for specifically influencing the growth of the plants.

As a rule, the fungicidal compositions according to the invention comprise between 0.001 and 95 per cent by weight of compound according to the invention or compounds according to the invention as active ingredient(s), depending on the type of the compositions. They can be in a form which is suitable for storage and for transport. The active ingredient concentration in such forms, for example in emulsifiable concentrates is generally in the upper range of the above concentration interval. These forms can then be diluted with identical or different formulation auxiliaries to active ingredient concentrations which are suitable for practical usage, such concentrations are generally in the lower range of the above concentration interval. As a rule, emulsifiable concentrates comprise 5 to 85 per cent by weight, preferably 25 to 75 per cent by weight, of the compound(s) according to the invention. Suitable use forms are, inter alia, ready-for-use solutions, emulsions and suspensions which are suitable, for example, as spray mixtures. The concentrations in such spray mixtures can be, for example, between 0.0001 and 20 per cent by weight. The ultra-low-volume method allows spray mixtures to be formulated in which the active ingredient concentration is preferably 0.5 to 20 per cent by weight, while the active ingredient concentration of spray mixtures formulated in the low-volume method and in the high-volume method are preferably 0.02 to 1.0 and 0.002 to 0.1 per cent by weight, respectively.

The fungicidal compositions according to the invention can be prepared by mixing at least one compound according to the invention with formulation auxiliaries.

The compositions can be prepared in a known manner, for example by mixing the active ingredients with solid carriers, by dissolving or suspending them in suitable solvents or dispersants, if appropriate using surfactants as wetting agents or emulsifiers, or using dispersants, or by diluting preformulated emulsifiable concentrates with solvents or dispersants, and the like.

In the case of compositions in the form of powders, the active ingredient can be mixed with a solid carrier, for example by grinding the mixture; or the solid carrier can be impregnated with a solution or suspension of the active ingredient, and the solvent, or dispersant, can then be removed by evaporation, heating or by filtration with suction under reduced pressure. Such compositions in the form of powders can be made readily wettable with water by an addition of surfactants or dispersants, so that they can be converted into aqueous suspensions which are suitable, for example, as sprays.

Alternatively, the compounds according to the invention can be mixed with a surfactant and a solid carrier to give a wettable powder which is dispersible in water, or they can be mixed with a solid pregranulated carrier to give a product in the form of granules.

If desired, a compound according to the invention can be dissolved in a solvent which is not miscible with water, for example an alicyclic ketone, which expediently comprises dissolved emulsifier, so that a self-emulsifying effect of the solution is obtained when water is added. Moreover, the active ingredient can be mixed with an emulsifier, and the mixture can then be diluted with water to the desired concentration. The active ingredient can furthermore be dissolved in a solvent and the solution then mixed with an emulsifier. Such a mixture can also be diluted with water to the desired concentration. In this manner, emulsifiable concentrates, or ready-for-use emulsions, are obtained.

The compound of the compositions according to the invention can be applied by the application methods conventionally used in crop protection or in agriculture. The method according to the invention for the control of fungi comprises treating the material to be protected, for example plants, parts of plants or seeds, with an effective amount of a compound according to the invention or of a composition according to the invention.

The examples hereinafter illustrate the invention without imposing any limitation.

PREPARATION EXAMPLES

Example H-1:1.43 g of methyl 2-(α-bromo-o-tolyl)-3-methyloxyacrylate and 0.82 g of 1-(phenylazo)acetaldoxime are added to a suspension of 120 mg of sodium hydride in 10 ml of N,N-dimethylformamide. The reaction mixture is stirred for 30 minutes under a nitrogen atmosphere, poured into ice-water and extracted twice using ethyl acetate. The combined organic phases are dried over anhydrous sodium sulfate and concentrated. The orange, oily residue is purified by chromatography on silica gel using ethyl acetate/hexane (1:2) as eluent and crystallised from diethyl ether/hexane in the refrigerator. This gives methyl 3-methoxy-2-[(1-[1-phenylazo]ethylideneaminooxy)-o-tolyl]acrylate in the form of orange crystals which melt at 72°–73° C.

Examples H-2 to H-390:The compounds listed in Table 1 can be prepared analogously to the procedure described in Example H-1.

TABLE 1

| Ex. | X | R₁ | R₂ | Physical data m.p. °C. ¹H-NMR [δ in ppm] |
|---|---|---|---|---|
| H-1 | CH | methyl | phenyl | 72–73 |
| H-2 | N | methyl | phenyl | 119–120 |
| H-3 | CH | H | phenyl | 90–92 |
| H-4 | CH | methyl | 3-fluorophenyl | 82–83 |
| H-5 | N | methyl | 3-fluorophenyl | |
| H-6 | CH | methyl | 4-fluorophenyl | 93–94 |
| H-7 | N | methyl | 4-fluorophenyl | 109–110 |
| H-8 | CH | methyl | 2-chlorophenyl | 112–113 isomer A 78–80 isomer B |
| H-9 | N | methyl | 2-chlorophenyl | |
| H-10 | CH | methyl | 3-chlorophenyl | 85–86 |
| H-11 | CH | H | 3-chlorophenyl | 77–80 |
| H-12 | CH | methyl | 4-chlorophenyl | 7.62(OCH=); 5.36(CH₂) |
| H-13 | N | methyl | 4-chlorophenyl | |
| H-14 | CH | methyl | 3-bromophenyl | 80–82 |
| H-15 | N | H | 3-bromophenyl | |
| H-16 | CH | methyl | 4-bromophenyl | 132–133 |
| H-17 | N | cyclopropyl | 4-bromophenyl | |
| H-18 | CH | methyl | 3,4-difluorophenyl | |
| H-19 | N | methyl | 3,4-difluorophenyl | |
| H-20 | CH | methyl | 3,5-difluorophenyl | |
| H-21 | N | methyl | 3,5-difluorophenyl | |
| H-22 | CH | methyl | 3,4-dichlorophenyl | 91–92 |
| H-23 | N | H | 3,4-dichlorophenyl | |
| H-24 | CH | methyl | 3,5-dichlorophenyl | 101–102 |
| H-25 | N | H | 3,5-dichlorophenyl | |
| H-26 | CH | methyl | 3-Cl, 4-F-phenyl | 96–98 |
| H-27 | N | methyl | 3-Cl, 4-F-phenyl | |
| H-28 | CH | cyclopropyl | 4-Cl, 2-F-phenyl | |
| H-29 | N | methyl | 4-Cl, 2-F-phenyl | |
| H-30 | CH | H | 3,4,5-trichlorophenyl | |
| H-31 | N | methyl | 3,4,5-trichlorophenyl | |
| H-32 | CH | methyl | 2,4,5-trichlorophenyl | |
| H-33 | N | methyl | 2,4,5-trichlorophenyl | |
| H-34 | CH | methyl | 1-naphthyl | |
| H-35 | N | methyl | 1-naphthyl | |
| H-36 | CH | methyl | 2-naphthyl | |
| H-37 | N | methyl | 2-naphthyl | |
| H-38 | CH | cyclopropyl | 2-methylphenyl | |
| H-39 | CH | methyl | 2-methylphenyl | 78–80 |
| H-40 | CH | methyl | 3-methylphenyl | 77–78 |
| H-41 | N | methyl | 3-methylphenyl | 101–102 |
| H-42 | CH | methyl | 4-methylphenyl | 97–99 |
| H-43 | N | H | 4-methylphenyl | |
| H-44 | CH | methyl | 2,3-dimethylphenyl | |
| H-45 | N | methyl | 2,3-dimethylphenyl | |
| H-46 | CH | methyl | 2,4-dimethylphenyl | |
| H-47 | N | cyclopropyl | 2,4-dimethylphenyl | |
| H-48 | CH | methyl | 2,5-dimethylphenyl | |
| H-49 | N | methyl | 2,5-dimethylphenyl | |
| H-50 | CH | H | 3,4-dimethylphenyl | |
| H-51 | N | methyl | 3,4-dimethylphenyl | |
| H-52 | CH | methyl | 3,5-dimethylphenyl | |
| H-53 | N | methyl | 3,5-dimethylphenyl | |
| H-54 | CH | methyl | 3-methoxyphenyl | |
| H-55 | N | methyl | 3-methoxyphenyl | |
| H-56 | CH | methyl | 4-methoxyphenyl | 78–84 |
| H-57 | N | cyclopropyl | 4-methoxyphenyl | |
| H-58 | CH | methyl | 3,4-dimethoxyphenyl | |
| H-59 | N | methyl | 3,4-dimethoxyphenyl | |
| H-60 | CH | methyl | 3,5-dimethoxyphenyl | |
| H-61 | N | cyclopropyl | 3,5-dimethoxyphenyl | |
| H-62 | CH | methyl | 3,4-methylenedioxyphenyl | |
| H-63 | N | methyl | 3,4-methylenedioxyphenyl | |
| H-64 | CH | methyl | 3,4-ethylenedioxyphenyl | 101–104 |
| H-65 | N | methyl | 3,4-ethylenedioxyphenyl | |

TABLE 1-continued

| Ex. | X | R₁ | R₂ | Physical data m.p. °C. ¹H-NMR [δ in ppm] |
|---|---|---|---|---|
| H-66 | CH | methyl | 2,2-difluoro-5-benzodioxolyl | |
| H-67 | N | methyl | 2,2-difluoro-5-benzodioxolyl | |
| H-68 | CH | methyl | 3-trifluoromethoxyphenyl | |
| H-69 | N | methyl | 3-trifluoromethoxyphenyl | |
| H-70 | CH | methyl | 4-trifluoromethoxyphenyl | 7.62(OCH=) 5.37(CH₂) |
| H-71 | N | H | 4-trifluoromethoxyphenyl | |
| H-72 | CH | methyl | 3-trifluoromethylphenyl | 7.62(OCH=) 5.39(CH₂) |
| H-73 | N | methyl | 3-trifluoromethylphenyl | |
| H-74 | CH | methyl | 4-trifluoromethylphenyl | 109–110 |
| H-75 | N | H | 4-trifluoromethylphenyl | |
| H-76 | CH | methyl | 3,5-bis-(trifluoromethyl)-phenyl | 117–118 |
| H-77 | N | methyl | 3,5-bis-(trifluoromethyl)-phenyl | |
| H-78 | CH | methyl | 4-F, 3-CF₃-phenyl | |
| H-79 | N | methyl | 4-F, 3-CF₃-phenyl | |
| H-80 | CH | methyl | 4-Cl, 3-CF₃-phenyl | |
| H-81 | N | cyclopropyl | 4-Cl, 3-CF₃-phenyl | |
| H-82 | CH | methyl | 3-acetylphenyl | |
| H-83 | N | methyl | 3-acetylphenyl | |
| H-84 | CH | cyclopropyl | 4-acetylphenyl | |
| H-85 | N | methyl | 4-acetylphenyl | |
| H-86 | CH | methyl | 3-carboxyphenyl | |
| H-87 | N | H | 3-carboxyphenyl | |
| H-88 | CH | methyl | 4-carboxyphenyl | |
| H-89 | N | methyl | 4-carboxyphenyl | |
| H-90 | CH | methyl | 3-carbethoxyphenyl | |
| H-91 | N | methyl | 3-carbethoxyphenyl | |
| H-92 | CH | methyl | 4-carbethoxyphenyl | |
| H-93 | N | methyl | 4-carbethoxyphenyl | |
| H-94 | CH | methyl | 3-cyanophenyl | |
| H-95 | N | methyl | 3-cyanophenyl | |
| H-96 | CH | H | 4-cyanophenyl | |
| H-97 | N | H | 4-cyanophenyl | |
| H-98 | CH | methyl | 4-cyanomethylphenyl | |
| H-99 | CH | methyl | 4-biphenylyl | |
| H-100 | CH | methyl | 4-carboxy-3-chlorophenyl | |
| H-101 | CH | H | 3-carboxy-4-chlorophenyl | |
| H-102 | CH | methyl | 3-chloro-4-cyanophenyl | |
| H-103 | CH | methyl | 2-fluorenyl | |
| H-104 | CH | methyl | 3-benzyloxyphenyl | |
| H-105 | N | methyl | 3-benzyloxyphenyl | |
| H-106 | CH | H | 4-benzyloxyphenyl | |
| H-107 | N | methyl | 4-benzyloxyphenyl | |
| H-108 | CH | methyl | 4-bromo-2-fluorophenyl | |
| H-109 | N | methyl | 4-bromo-2-fluorophenyl | |
| H-110 | CH | cyclopropyl | 4-bromo-3-methylphenyl | |
| H-111 | N | methyl | 4-bromo-3-methylphenyl | |
| H-112 | CH | methyl | 6-(2,2-difluoro-1,4-benzodioxanyl) | |
| H-113 | CH | methyl | 6-(2,2,3-trifluoro-1,4-benzodioxanyl) | |
| H-114 | CH | methyl | 3-F, 5-CF₃-phenyl | |
| H-115 | N | methyl | 3-F, 5-CF₃-phenyl | |
| H-116 | CH | methyl | 2-F, 5-CF₃-phenyl | |
| H-117 | CH | cyclopropyl | 3-CH₃O, 5-CF₃-phenyl | |
| H-118 | N | methyl | 3-CH₃O, 5-CF₃-phenyl | |
| H-119 | CH | methyl | 3-NO₂, 5-CF₃-phenyl | |
| H-120 | N | methyl | 3-NO₂, 5-CF₃-phenyl | |
| H-121 | CH | H | 4-Br, 3-CF₃-phenyl | |
| H-122 | N | methyl | 4-Br, 3-CF₃-phenyl | |
| H-123 | CH | methyl | 4-tert-butylphenyl | 105–108 |
| H-124 | CH | cyclopropyl | 4-sec-butylphenyl | |
| H-125 | CH | methyl | 4-butylphenyl | |
| H-126 | CH | methyl | 4-butoxyphenyl | |
| H-127 | CH | methyl | 3-Cl, 4-MeO-phenyl | |
| H-128 | N | methyl | 3-Cl, 4-MeO-phenyl | |
| H-129 | CH | methyl | 3-Cl, 4-Me-phenyl | 97–98 |
| H-130 | N | H | 3-Cl, 4-Me-phenyl | |
| H-131 | CH | H | 4-Cl, 2-Me-phenyl | |
| H-132 | CH | methyl | 5-Cl, 2-Me-phenyl | |
| H-133 | CH | methyl | 4-Cl, 3-NO₂-phenyl | |

TABLE 1-continued

| Ex. | X | R₁ | R₂ | Physical data m.p. °C. ¹H-NMR [δ in ppm] |
|---|---|---|---|---|
| H-134 | N | cyclopropyl | 4-Cl, 3-NO₂-phenyl | |
| H-135 | CH | methyl | 4-cyclohexylphenyl | |
| H-136 | N | methyl | 4-cyclohexylphenyl | |
| H-137 | CH | methyl | 5-indanyl | |
| H-138 | N | cyclopropyl | 5-indanyl | |
| H-139 | CH | methyl | 3,5-dinitrophenyl | |
| H-140 | N | methyl | 3,5-dinitrophenyl | |
| H-141 | CH | H | 2-nitrophenyl | |
| H-142 | N | methyl | 2-nitrophenyl | |
| H-143 | CH | methyl | 3-nitrophenyl | 90–92 |
| H-144 | N | methyl | 3-nitrophenyl | |
| H-145 | CH | H | 4-nitrophenyl | |
| H-146 | N | methyl | 4-nitrophenyl | |
| H-147 | CH | methyl | 3-ethylphenyl | |
| H-148 | CH | H | 4-ethylphenyl | |
| H-149 | CH | H | 3-ethoxyphenyl | |
| H-150 | CH | methyl | 4-ethoxyphenyl | |
| H-151 | CH | methyl | 3-F, 4-CH₃O-phenyl | |
| H-152 | CH | methyl | 3-F, 4-CH₃-phenyl | |
| H-153 | N | methyl | 3-F, 4-CH₃-phenyl | |
| H-154 | CH | methyl | 4-F, 3-NO₂-phenyl | |
| H-155 | N | methyl | 4-F, 3-NO₂-phenyl | |
| H-156 | CH | methyl | 4-isopropylphenyl | 95–97 |
| H-157 | CH | methyl | 3-iodophenyl | |
| H-158 | N | cyclopropyl | 3-iodophenyl | |
| H-159 | CH | methyl | 4-iodophenyl | |
| H-160 | N | methyl | 4-iodophenyl | |
| H-161 | CH | methyl | 3-mercaptophenyl | |
| H-162 | N | methyl | 3-mercaptophenyl | |
| H-163 | CH | methyl | 4-mercaptophenyl | |
| H-164 | N | H | 4-mercaptophenyl | |
| H-165 | CH | methyl | 3-methylmercaptophenyl | |
| H-166 | N | methyl | 3-methylmercaptophenyl | |
| H-167 | CH | cyclopropyl | 4-methylmercaptophenyl | |
| H-168 | N | methyl | 4-methylmercaptophenyl | |
| H-169 | CH | methyl | 4-CH₃, 3-NO₂-phenyl | |
| H-170 | N | H | 4-CH₃, 3-NO₂-phenyl | |
| H-171 | CH | methyl | 4-CH₃, 2-NO₂-phenyl | |
| H-172 | CH | methyl | 2-CH₃, 5-NO₂-phenyl | |
| H-173 | CH | cyclopropyl | 2-CH₃, 4-NO₂-phenyl | |
| H-174 | CH | methyl | 4-(4-morpholino)phenyl | |
| H-175 | N | methyl | 4-(4-morpholino)phenyl | |
| H-176 | CH | H | 4-phenoxyphenyl | |
| H-177 | N | methyl | 4-phenoxyphenyl | |
| H-178 | CH | methyl | 4-propylphenyl | |
| H-179 | N | methyl | 4-propylphenyl | |
| H-180 | CH | methyl | 4-sulfamoylphenyl | 143 |
| H-181 | CH | methyl | 5,6,7,8-tetrahydro-1-naphthyl | |
| H-182 | CH | methyl | 2,3,4-trichlorophenyl | |
| H-183 | N | H | 2,3,4-trichlorophenyl | |
| H-184 | CH | methyl | 2-trifluoromethylphenyl | |
| H-185 | N | methyl | 2-trifluoromethylphenyl | |
| H-186 | CH | methyl | 3,4,5-trimethoxyphenyl | |
| H-187 | CH | methyl | 2-pyridyl | 79–80 |
| H-188 | N | methyl | 2-pyridyl | 128–129 |
| H-189 | CH | methyl | 3-pyridyl | |
| H-190 | N | H | 3-pyridyl | |
| H-191 | CH | methyl | 4-pyridyl | |
| H-192 | N | cyclopropyl | 4-pyridyl | |
| H-193 | CH | methyl | 2-pyrimidinyl | |
| H-194 | N | methyl | 2-pyrimidinyl | |
| H-195 | CH | methyl | 4-pyrimidinyl | |
| H-196 | N | H | 4-pyrimidinyl | |
| H-197 | CH | methyl | pyrazinyl | |
| H-198 | N | methyl | pyrazinyl | |
| H-199 | CH | methyl | 2-quinolinyl | |
| H-200 | N | methyl | 2-quinolinyl | |
| H-201 | CH | cyclopropyl | 3-quinolinyl | |
| H-202 | N | methyl | 3-quinolinyl | |
| H-203 | CH | H | 4-quinolinyl | |
| H-204 | N | methyl | 4-quinolinyl | |
| H-205 | CH | methyl | 5-quinolinyl | |
| H-206 | N | methyl | 5-quinolinyl | |

TABLE 1-continued

| Ex. | X | R₁ | R₂ | Physical data m.p. °C. ¹H-NMR [δ in ppm] |
|---|---|---|---|---|
| H-207 | CH | methyl | 6-quinolinyl | |
| H-208 | N | cyclopropyl | 6-quinolinyl | |
| H-209 | CH | methyl | 8-quinolinyl | |
| H-210 | N | H | 8-quinolinyl | |
| H-211 | CH | methyl | 1-isoquinolinyl | |
| H-212 | CH | methyl | 5-isoquinolinyl | |
| H-213 | CH | methyl | 3-pyrazolyl | |
| H-214 | N | methyl | 3-pyrazolyl | |
| H-215 | CH | methyl | 2-benzimidazolyl | |
| H-216 | N | cyclopropyl | 2-benzimidazolyl | |
| H-217 | CH | methyl | 3,4-benzocoumarin-6-yl | |
| H-218 | N | methyl | 3,4-benzocoumarin-6-yl | |
| H-219 | CH | methyl | 2,1,3-benzothiadiazol-4-yl | |
| H-220 | N | methyl | 2,1,3-benzothiadiazol-4-yl | |
| H-221 | CH | methyl | 2-benzothiazolyl | |
| H-222 | N | cyclopropyl | 2-benzothiazolyl | |
| H-223 | CH | methyl | 3-benzyloxy-2-pyridyl | |
| H-224 | CH | methyl | 5-bromo-2-pyridyl | |
| H-225 | N | H | 5-bromo-2-pyridyl | |
| H-226 | CH | methyl | 5-bromo-2-pyrimidinyl | |
| H-227 | N | methyl | 5-bromo-2-pyrimidinyl | |
| H-228 | CH | methyl | 5-bromo-2-thiazolyl | |
| H-229 | N | H | 5-bromo-2-thiazolyl | |
| H-230 | CH | methyl | 2-methyl-4-quinolinyl | |
| H-231 | N | methyl | 2-methyl-4-quinolinyl | |
| H-232 | CH | methyl | 4-chloro-2-benzothiazolyl | |
| H-233 | N | methyl | 4-chloro-2-benzothiazolyl | |
| H-234 | CH | methyl | 6-chloro-2-benzothiazolyl | |
| H-235 | N | methyl | 6-chloro-2-benzothiazolyl | |
| H-236 | CH | methyl | 5-chloro-2-benzoxazolyl | |
| H-237 | N | cyclopropyl | 5-chloro-2-benzoxazolyl | |
| H-238 | CH | methyl | 6-chloro-2-methylmercapto-4-pyrimidinyl | |
| H-239 | CH | H | 4-chloro-6-methyl-2-pyrimidinyl | |
| H-240 | N | methyl | 4-chloro-6-methyl-2-pyrimidinyl | |
| H-241 | CH | methyl | 6-chloro-3-nitro-2-pyridyl | |
| H-242 | CH | methyl | 4-(4-chlorophenyl)-2-thiazolyl | |
| H-243 | N | H | 4-(4-chlorophenyl)-2-thiazolyl | |
| H-244 | CH | methyl | 6-chloro-2-purinyl | |
| H-245 | CH | methyl | 5-chloro-2-pyridyl | |
| H-246 | N | H | 5-chloro-2-pyridyl | |
| H-247 | CH | methyl | 2-chloro-3-pyridyl | |
| H-248 | N | methyl | 2-chloro-3-pyridyl | |
| H-249 | CH | methyl | 2-chloro-5-pyridyl | |
| H-250 | N | cyclopropyl | 2-chloro-5-pyridyl | |
| H-251 | CH | methyl | 4-cyano-3-pyrazolyl | |
| H-252 | N | methyl | 4-cyano-3-pyrazolyl | |
| H-253 | CH | methyl | 3,5-dichloro-2-pyridyl | |
| H-254 | CH | methyl | 4,6-dichloro-2-pyrimidinyl | |
| H-255 | N | cyclopropyl | 4,6-dichloro-2-pyrimidinyl | |
| H-256 | CH | H | 2,6-dimethoxy-3-pyridyl | |
| H-257 | CH | methyl | 6-chloro-3-pyridazinyl | |
| H-258 | N | methyl | 6-chloro-3-pyridazinyl | |
| H-259 | CH | methyl | 6-trifluoromethyl-2-pyridyl | 7.60(OCH=) 5.42(CH₂) |
| H-260 | N | H | 6-trifluoromethyl-2-pyridyl | |
| H-261 | CH | methyl | 6-methyl-4-trifluoromethyl-2-pyridyl | 141–142 |
| H-262 | N | methyl | 6-methyl-4-trifluoromethyl-2-pyridyl | |
| H-263 | CH | methyl | 5-methoxycarbonyl-4-trifluoromethyl-2-pyrimidinyl | |
| H-264 | CH | methyl | 3-methyl-6-pyridazinyl | |
| H-265 | CH | methyl | 1,3,4-trimethyl-1H-pyrazolo-[3,4-b]pyrid-6-yl | |
| H-266 | CH | methyl | 5,6-dimethyl-2-benzothiazolyl | |
| H-267 | CH | methyl | 2,4-dimethyl-1,8-naphthyridin-7-yl | |
| H-268 | CH | H | 4,6-dimethyl-2-pyridyl | |
| H-269 | CH | methyl | 4,6-dimethyl-2-pyrimidinyl | |
| H-270 | CH | methyl | 2,6-dimethyl-4-pyrimidinyl | |
| H-271 | CH | cyclopropyl | 4,5-dimethyl-2-thiazolyl | |
| H-272 | CH | methyl | 5,6-dimethyl-1,2,4-triazin-3-yl | |
| H-273 | CH | methyl | 6-ethoxy-2-benzothiazolyl | |

TABLE 1-continued

| Ex. | X | R₁ | R₂ | Physical data m.p. °C. ¹H-NMR [δ in ppm] |
|---|---|---|---|---|
| H-274 | CH | methyl | 9-ethyl-3-carbazolyl | |
| H-275 | CH | methyl | 5-(ethylmercapto)-1,3,4-thiadiazol-2-yl | |
| H-276 | CH | H | 1-ethyl-5-pyrazolyl | |
| H-277 | CH | methyl | 2-ethyl-1,3,4-thiadiazol-5-yl | |
| H-278 | CH | methyl | 6-fluoro-2-benzothiazolyl | |
| H-279 | CH | methyl | 5-indazolyl | |
| H-280 | CH | methyl | 6-indazolyl | |
| H-281 | CH | methyl | 5-indolyl | |
| H-282 | CH | methyl | 4-methoxy-2-benzothiazolyl | |
| H-283 | CH | methyl | 6-methoxy-2-benzothiazolyl | |
| H-284 | CH | H | 2-methoxy-5-pyridyl | |
| H-285 | CH | cyclopropyl | 4-methyl-2-benzothiazolyl | |
| H-286 | CH | methyl | 6-methyl-2-benzothiazolyl | |
| H-287 | CH | methyl | 2-methyl-5-benzothiazolyl | |
| H-288 | CH | methyl | 3-methyl-5-isothiazolyl | |
| H-289 | CH | H | 5-methyl-3-isoxazolyl | |
| H-290 | CH | methyl | 4-methyl-5-nitro-2-pyridyl | |
| H-291 | CH | methyl | 4-methyl-2-pyrimidinyl | |
| H-292 | CH | methyl | 5-methyl-1,3,4-thiadiazol-2-yl | |
| H-293 | CH | cyclopropyl | 4-methyl-2-thiazolyl | |
| H-294 | CH | methyl | 3-carboxy-6-pyridyl | |
| H-295 | CH | methyl | 3-carbamoyl-6-pyridyl | |
| H-296 | CH | methyl | 6-nitro-2-benzothiazolyl | |
| H-297 | CH | methyl | 5-nitro-2-pyridyl | |
| H-298 | CH | methyl | 5-nitro-2-pyrimidinyl | |
| H-299 | CH | methyl | 5-nitro-2-thiazolyl | |
| H-300 | CH | H | 4-phenyl-2-thiazolyl | |
| H-301 | CH | methyl | 4-methyl-2-pyridyl | |
| H-302 | CH | methyl | 6-methyl-2-pyridyl | |
| H-303 | CH | methyl | 5-methyl-2-pyridyl | |
| H-304 | CH | methyl | 2-purinyl | |
| H-305 | CH | methyl | 4-cyano-3-pyrazolyl | |
| H-306 | CH | methyl | 2,3,5,6-tetrafluoro-4-pyridyl | |
| H-307 | CH | methyl | 5-tetrazolyl | |
| H-308 | N | methyl | 5-tetrazolyl | |
| H-309 | CH | methyl | 1,3,4-thiadiazol-2-yl | |
| H-310 | N | H | 1,3,4-thiadiazol-2-yl | |
| H-311 | CH | methyl | 2-thiazolyl | |
| H-312 | N | cyclopropyl | 2-thiazolyl | |
| H-313 | CH | methyl | 1,2,4-triazin-3-yl | |
| H-314 | N | methyl | 1,2,4-triazin-3-yl | |
| H-315 | CH | methyl | 1H-1,2,4-triazol-3-yl | |
| H-316 | CH | methyl | 5-trifluoromethyl-1,3,4-thiadiazol-2-yl | |
| H-317 | CH | methyl | 1-phthalazinyl | |
| H-318 | CH | methyl | 2-(4-bromophenoxy)-5-pyridyl | |
| H-319 | CH | methyl | 2-(4-chlorophenoxy)-5-pyridyl | |
| H-320 | CH | cyclopropyl | 2-(3-chlorophenoxy)-5-pyridyl | |
| H-321 | CH | methyl | 3-cyclopropyl-1-methyl-5-pyrazolyl | |
| H-322 | CH | methyl | 5-cyclopropyl-1,3,4-thiadiazol-2-yl | |
| H-323 | CH | methyl | 4,6-dimethyl-1,3,5-triazin-2-yl | |
| H-324 | CH | methyl | 3-methyl-5-isoxazolyl | |
| H-325 | CH | H | 2-methyl-3-pyrazolyl | |
| H-326 | CH | methyl | 7-chloro-4-quinolinyl | |
| H-327 | N | methyl | 7-chloro-4-quinolinyl | |
| H-328 | CH | methyl | 2-methoxycarbonyl-3-thienyl | |
| H-329 | CH | ethyl | phenyl | |
| H-330 | N | ethyl | phenyl | |
| H-331 | CH | ethyl | 2-pyridyl | |
| H-332 | N | ethyl | 2-pyridyl | |
| H-333 | CH | propyl | phenyl | |
| H-334 | N | propyl | phenyl | |
| H-335 | CH | propyl | 2-pyridyl | |
| H-336 | N | propyl | 2-pyridyl | |
| H-337 | CH | isopropyl | phenyl | |
| H-338 | N | isopropyl | phenyl | |
| H-339 | CH | isopropyl | 2-pyridyl | |
| H-340 | N | isopropyl | 2-pyridyl | |
| H-341 | CH | trifluoromethyl | phenyl | |
| H-342 | N | trifluoromethyl | phenyl | |
| H-343 | CH | trifluoro- | 2-pyridyl | |

TABLE 1-continued

| Ex. | X | R$_1$ | R$_2$ | Physical data m.p. °C. $^1$H-NMR [δ in ppm] |
|---|---|---|---|---|
| H-344 | N | methyl trifluoro- methyl | 2-pyridyl | |

Examples F-1.1 to F-6.3: Formulation of compounds to the invention

Examples F-1.1 to F-1.3: Emulsion concentrates

| Components | F-1.1 | F-1.2 | F-1.3 |
|---|---|---|---|
| Active ingredient from the table | 25% | 40% | 50% |
| Calcium dodecylbenzenesulfonate | 5% | 8% | 6% |
| Castor oil polyethylene glycol ether (36 mol of ethylenoxy units) | 5% | — | — |
| Tributylphenol polyethylene glycol ether (30 mol of ethylenoxy units) | — | 12% | 4% |
| Cyclohexanone | — | 15% | 20% |
| Xylene mixture | 65% | 25% | 20% |

Emulsions of any desired lower concentration can be prepared from these emulsion concentrates by dilution with water.

Example F-2: Emulsion concentrate

| Components | F-2 |
|---|---|
| Active ingredient from the table | 10% |
| Octylphenol polyethylene glycol ether (4 to 5 mol of ethylenoxy units) | 3% |
| Calcium dodecylbenzenesulfonate | 3% |
| Castor oil polyglycol ether (36 mol of ethylenoxy units) | 4% |
| Cyclohexanone | 30% |
| Xylene mixture | 50% |

Emulsions of any desired lower concentration can be prepared from this emulsion concentrate by dilution with water.

Examples F-3.1 to F-3.4: Solutions

| Components | F-3.1 | F-3.2 | F-3.3 | F-3.4 |
|---|---|---|---|---|
| Active ingredient from the table | 80% | 10% | 5% | 95% |
| Propylene glycol monomethyl ether | 20% | — | — | — |
| Polyethylene glycol (relative molecular weight: 400 atomic mass units) | — | 70% | — | — |
| N-Methylpyrrolid-2-one | — | 20% | — | — |
| Epoxidised coconut oil | — | — | 1% | 5% |
| Petroleum spirit (boiling range: 160–90°) | — | — | 94% | — |

The solutions are suitable for use in the form of microdrops.

Examples F-4.1 to F-4.4: Granules

| Components | F-4.1 | F-4.2 | F-4.3 | F-4.4 |
|---|---|---|---|---|
| Active ingredient from the table | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient according to the invention is dissolved in dichloromethane, the solution is sprayed onto the carrier, and the solvent is subsequently removed by evaporation in vacuo.

Examples F-5.1 and F-5.2: Dusting agents

| Components | F-5.1 | F-5.2 |
|---|---|---|
| Active ingredient from the table | 2% | 5% |
| Highly disperse silica | 1% | 5% |
| Talc | 97% | — |
| Kaolin | — | 90% |

Ready-for-use dusting agents are obtained by intimately mixing all components.

Examples F-6.1 to F-6.3: Wettable powders

| Components | F-6.1 | F-6.2 | F-6.3 |
|---|---|---|---|
| Active ingredient from the table | 25% | 50% | 75% |
| Sodium ligninsulfonate | 5% | 5% | — |
| Sodium lauryl sulfate | 3% | — | 5% |
| Sodium diisobutylnaphthalene-sulfonate | — | 6% | 10% |
| Octylphenol polyethylene glycol ether (7 to 8 mol of ethylenoxy units) | — | 2% | — |
| Highly disperse silica | 5% | 10% | 10% |
| Kaolin | 62% | 27% | — |

All components are mixed thoroughly, and the mixture is ground thoroughly in a suitable mill. This gives wettable powders from which suspensions of any desired concentration can be prepared by mixing them with water.

Examples B-1 to B-9: Biological activity of compounds according to the invention Example B-1: Activity against Botrytis cinerea on beans. Residual protective activity Bean plants approx. 10 cm in height are sprayed with a spray mixture (0.02% of active ingredient) prepared with a wettable powder of the active ingredient. After 48 hours, the treated plants are infected with a conidia suspension of the fungus. The fungus infestation is rated after incubation of the infected plant for 3 days at 95–100% relative atmospheric humidity and 21° C.

The Botrytis infestation of untreated, but infected bean plants was 100%. The infestation after treatment with one of the compounds of the formula I was <20%.

Example B-2: Activity against Puccinia graminis on wheat a) Residual protective activity Test method: 6 days after sowing, wheat plants are sprayed to drip point with an aqueous spray mixture (0.02% of active ingredient) prepared with a wettable powder comprising one of the active ingredients according to the invention and, 24 hours later, infected with a ureidospore suspension of the fungus. After an incubation time of 48 hours (conditions: 95 to 100 per cent relative atmospheric humidity at 20°), the plants are placed in a greenhouse at 22°. The activity of the active ingredient is assessed on the basis of a rating of the rust pustule development 12 days after infection.

b) Systemic activity

Test method: An aqueous spray mixture (0.006% of active ingredient, relative to the soil volume) prepared with a wettable powder comprising one of the active ingredients according to the invention is poured next to wheat plants 5 days after sowing. Care is taken that the spray mixture does not come in contact with aerial parts of the plant. 48 hours later, the plants are infected with a ureidospore suspension of the fungus. After an incubation time of 48 hours (conditions: 95 to 100 per cent relative atmospheric humidity at 20°), the plants are placed in a greenhouse at 22°. The activity of the active ingredient is assessed on the basis of a rating of the rust pustule development 12 days after infection.

Test result: Active ingredients according to the invention exhibit a good residual-protective activity against Puccinia graminis on wheat, for example the active ingredients according to Examples H-1, H-2, H-6, H-7, H-12, H-24, H-39, H-40, H-41 and H-76 reduce fungus infestation to 20 to 5%. In contrast, the fungus infestation of infected control plants which have not been treated with the active ingredient is 100%.

Example B-3: Activity against *Phytophthora infestans* on tomatoes a) Residual protective activity Test method: Tomato plants are grown for three weeks, sprayed to drip point with an aqueous spray mixture (0.02% active ingredient) prepared with a wettable powder comprising one of the active ingredients according to the invention and, 24 hours later, infected with a sporangia suspension of the fungus. The activity of the active ingredient is assessed on the basis of the rating of the fungus infestation 5 days after infection during which 90 to 100 per cent relative atmospheric humidity and a temperature of 20° are maintained.

Test result: Active ingredients according to the invention exhibit a good residual protective activity against *Phytophthora infestans* on tomatoes, for example the active ingredients according to Examples H-1, H-2, H-6, H-7, H-12, H-24, H-39, H-187 and H-76 reduce the fungus infestation to 5 to 0% and the active ingredients according to Examples H-16, H-40 and H-188 to 20 to 5%. In contrast, the fungus infestation of infected control plants which have not been treated with the active ingredient is 100%.

b) Systemic activity

Test method: Tomato plants are grown for three weeks, and an aqueous spray mixture (0.006% of active ingredient relative to the soil volume) prepared with a wettable powder comprising one of the active ingredients according to the invention is poured next to the tomato plants. Care is taken that the spray mixture does not come in contact with aerial parts of the plants. After 48 hours, the plants are infected with a sporangia suspension of the fungus. The activity of the active ingredient is assessed on the basis of the rating of the fungus infestation 5 days after infection during which a relative atmospheric humidity of 90 to 100 per cent and a temperature of 20° are maintained.

Test result: Active ingredients according to the invention exhibit a good systemic activity against *Phytophthora infestans* on tomatoes.

Example B-4: Residual protective activity against *Cercospora arachidicola* on groundnuts Test method: Groundnut plants 10 to 15 cm in height are sprayed to drip point with an aqueous spray mixture (0.02% active ingredient) prepared with a wettable powder comprising one of the active ingredients according to the invention and, 48 hours later, infected with a conidia suspension of the fungus. The plants are incubated for 72 hours and 21° and high atmospheric humidity and then placed in a greenhouse until the typical lesions appear. The activity of the active ingredient is assessed 12 days after the infection on the basis of number and size of the lesions.

Test result: Active ingredients according to the invention exhibit a good residual-protective activity against *Cercospora arachidicola* on groundnuts, for example the active ingredients according to Examples H-1, H-2, H-12, H-16, H-39, H-41, H-70, H-187 and H-188 reduce the fungus infestation to 5 to 0% and the active ingredients according to Examples H-40 and H-76 to 20 to 5%. In contrast, the fungus infestation of infected control plants which have not been treated with the active ingredient is 100%.

Example B-5: Activity against Plasmopara viticola on vines

Residual protective activity

Test method: Vine seedlings in the 4- to 5-leaf stage are sprayed to drip point with an aqueous spray mixture (0.02% of active ingredient) prepared with a wettable powder comprising one of the active ingredients according to the invention and, 24 hours later, infected with a sporangia suspension of the fungus. The activity of the active ingredient is assessed on the basis of the rating of the fungus infestation 6 days after infection during which a relative atmospheric humidity of 95 to 100 per cent and a temperature of 20° are maintained.

Test result: Active ingredients according to the invention exhibit a good preventive residual-protective activity against *Plasmopara viticola* on vines, for example the active ingredients according to Examples H-1, H-2, H-12, H-16, H-39, H-40, H-41 and H-76 reduce the fungus infestation to 5 to 0% and the active ingredients according to Examples H-12, H-70 and H-188 to 20 to 5%. In contrast, the fungus infestation of infested control plants which have not been treated with the active ingredient is 100%.

Example B-6: Activity against *Rhizoctonia solani* (soil fungus on rice plants)

a) Protective local activity

Rice plants which are 12 days old are watered with a spray mixture (0.006% active ingredient) prepared with a formulation of the active ingredient, without wetting aerial parts of the plant. A suspension of mycelium and sclerotia of *R. solani* is placed on the soil surface so as to infect the treated plants. The fungus infestation on leaf sheaths, leaves and stalk is assessed after incubation for 6 days at 27° C. (day) and 23° C. (night) and 100% relative atmospheric humidity (humid chamber).

23 b.) Protective local foliar application

Rice plants which are 12 days old are sprayed with a spray mixture prepared with a formulation of the active ingredients. After one day, the treated plants are infected with a suspension of mycelium and sclerotia of R. solani. The fungus infestation on leaf sheaths, leaves and stalk is assessed after incubation for 6 days at 27° C. (day) and 23° C. (night) and 100% relative atmospheric humidity (humid chamber).

Compounds of Table 1 exhibit a good activity by inhibiting infestation with Rhizoctonia. In contrast, the infestation of untreated, but infected control plants was 100%.

Example B-7: Residual protective activity against *Venmria inaequalis* on apples Test method: Apple cuttings which have fresh shoots 10 to 20 cm in length are sprayed to drip point with an aqueous spray mixture (0.02% active ingredient) prepared with a wettable powder comprising one of the active ingredients according to the invention and, 24 hours later, infected with a conidia suspension of the fungus. The plants are incubated for 5 days at 90 to 100 per cent relative atmospheric humidity and placed in a greenhouse at 20° to 24° for a further 10 days. The activity of the active ingredient is assessed on the basis of the rating of the scab infestation 15 days after infection.

Test result: Active ingredients according to the invention exhibit a good residual protective activity against *Venturia inaequalis* on apples (less than 20% fungus infestation). The compounds Nos. H-13 and H-39 reduce the infestation to less than 10%.

Example B-8: Activity against *Erysiphe graminis* on barley a) Residual protective activity Test method: Barley plants approx. 8 cm in height are sprayed to drip point with an aqueous spray mixture (0.02% active ingredient) prepared with a wettable powder comprising one of the active ingredients according to the invention and, after 3 to 4 hours, dusted with conidia of the fungus. The infected plants are placed in a greenhouse at 22°. The activity of the active ingredient is assessed on the basis of the rating of the fungus infestation 10 days after infection.

b) Systemic activity

Test method: An aqueous spray mixture (0.002% active ingredient, relative to the soil volume) preprared with a wettable powder comprising one of the active ingredients according to the invention is poured on to barley plants approx. 8 cm in height. Care is taken that the spray mixture does not come into contact with aerial parts of the plants. 48 hours later, the plants are dusted with conidia of the fungus. The infected plants are placed in a greenhouse at 22°. The activity of the active ingredient is assessed on the basis of the rating of the fungus infestation 10 days after infection.

Test result: Active ingredients according to the invention exhibit a good residual protective activity against *Erysiphe graminis* on barley, with the fungus infestation reduced in some cases to 5–0% (for example, inter alia, Nos. H-13 and H-39). In contrast, the fungus infestation of infected control plants which have not been treated with the active ingredient is 100%.

Example B-9: Activity against *Colletotrichum lagenarium* on *Cucumis sativus L.* a) Cucumber plants are grown for 2 weeks and then sprayed with a spray mixture prepared with a wettable powder of the active ingredient (concentration: 200 ppm).

24

After 48 hours, the plants are infected with a spore suspension ($1.5 \cdot 10^5$ spores/ml) of the fungus and incubated for 36 hours at high atmospheric humidity and a temperature of 23° C. The incubation is then continued under ambient atmospheric humidity and at 22° to 23° C.

The protective activity is assessed on the basis of the fungus infestation 7–8 days after the infection.

b) Cucumber plants are grown for 2 weeks and then treated with a spray mixture prepared with a wettable powder of the active ingredient by means of soil application (concentration: 60 or 20 ppm relative to the soil volume). After 48 hours, the plants are infected with a spore suspension ($1.5 \cdot 10^5$ spores/ml) of the fungus and incubated for 36 hours at high atmospheric humidity and a temperature of 23° C. The incubation is then continued at ambient atmospheric humidity and at 22° C.

The protective activity is assessed on the basis of the fungus infestation 7–8 days after the infection.

Test result: in tests a) and b), active ingredients according to the invention exhibit a good activity against *Colletotrichum lagenarium*.

What is claimed is:

1. A compound of the formula I in form of a racemic mixture or isomer thereof

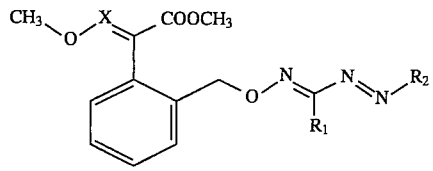

in which

X is CH or N, $R_1$ is hydrogen, $C_1$–$C_3$alkyl, trifluoromethyl or cyclopropyl, $R_2$ is aryl or heteroaryl, each of which is unsubstituted or substituted by one or more substituents R, R is halogen; $C_1$–$C_6$alkyl; $C_3$–$C_6$cycloalkyl; $C_1$–$C_4$haloalkyl; $C_1$–$C_4$alkoxy; hydroxyl; phenyl, benzyloxy or aryloxy, each of which is unsubstituted or substituted by halogen, $C_1$–$C_4$alkyl, $C_1$–$C_6$alkoxy, trifluoromethyl or trifluoromethoxy; $C_1$–$C_4$haloalkoxy; cyano; nitro; mercapto; $C_1$–$C_4$alkylthio; $NR_3R_4$; $CONR_3R_4$; cyanomethyl; $SO_2NR_3R_4$; $COR_5$ or $COOR_5$, $R_3$ and $R_4$ independently of one another are $C_1$–$C_4$alkyl or $R_3$ and $R_4$ together with the N atom form a 5–7-membered ring which can additionally contains 0–2 hetero atoms, and $R_5$ is hydroxyl, $C_1$–$C_4$alkyl or aryl.

2. A compound according to claim 1, in which X, $R_1$ and R are as defined above and $R_2$ is phenyl, naphthyl, tetrahydronaphthyl, indanyl or fluorenyl, each of which is unsubstituted or substituted by one or more R.

3. A compound according to claim 2, in which $R_2$ is phenyl which is unsubstituted or substituted by one or more R.

4. A compound according to claim 3, in which R is fluorine, chlorine, bromine, $C_1$–$C_4$alkyl, cyclopropyl, cyclohexyl, trifluoromethyl, trifluoromethoxy, $C_1$–$C_4$alkoxy, morpholino, cyano, cyanomethyl, nitro, phenyl, phenoxy, hydroxyl, benzyloxy or $C_1$–$C_2$alkylthio.

5. A compound according to claim 1, in which X, $R_1$ and R are as defined above and $R_2$, as heteroaryl, is a 5- or 6-membered heterocycle which has aromatic character and which is unsubstituted or substituted by one or more substituents R.

6. A compound according to claim 5, in which $R_2$ is pyridyl, pyrimidinyl, pyrazinyl, pyridazinyl or triazinyl, each of which is unsubstituted or substituted by one or more substituents R.

7. A compound according to claim 5, in which $R_2$ is pyrazolyl, thiazolyl, thiadiazolyl, thienyl, isothiazolyl, isoxazolyl, triazolyl or tetrazolyl, each of which is unsubstituted or substituted by one or more R.

8. A compound according to claim 1, in which X, $R_1$ and R are as defined above and $R_2$ is a heterocycle which is unsubstituted or substituted by one or more R and to which benzene is fused, or a phenyl group to which a heterocycle is fused.

9. A compound according to claim 8, in which $R_2$ is quinolinyl, isoquinolinyl, benzimidazolyl, benzothiazolyl, benzoxyazolyl, phthaiazinyl, benzocoumarinyl, benzothiadiazolyl, carbazyl, indolyl or indazolyl, each of which is unsubstituted or substituted by one or more R.

10. A compound according to claim 1, in which X, $R_1$ and R are as defined above and $R_2$ is methylenedioxyphenyl or ethylenedioxyphenyl, each of which is unsubstituted or substituted by one or more halogen, methyl or methoxy.

11. A compound according to claim 10, in which the methylene or ethylene bridge is substituted by fluorine.

12. A compound according to claim 1, in which X, $R_1$ and R are as defined above and $R_2$ is a heterocycle which is unsubstituted or substituted by one or more R and to which a second heterocycle is fused.

13. A compound according to claim 12, in which $R_2$ is purinyl, pteridinyl, pyrazolo[3,4-b]pyridyl or naphthyridinyl, each of which is unsubstituted or substituted by one or more R.

14. A compound according to claim 2, in which X is CH and $R_2$ is phenyl which is monosubstituted to trisubstituted by identical or different substituents from the group comprising halogen, $C_1$–$C_2$alkyl, $C_1$–$C_2$alkoxy, CN and $CF_3$.

15. A fungicidal composition which comprises, as active ingredient, a compound of the formula I according to claim 1 together with an inert carrier.

16. A composition according to claim 15 which comprises, as active ingredient, a compound according to claim 2.

17. A composition according to claim 15 which comprises, as active ingredient, a compound according to claim 14.

18. A method for controlling or preventing fungus infestation on plants, parts of plants or the locus where they are growing which comprises the application of a compound of the formula I according to claim 1.

19. A method according to claim 18 which comprises the application of a compound according to claim 2.

20. A method according to claim 18 which comprises the application of a compound according to claim 14.

21. A keto ester of formula VI

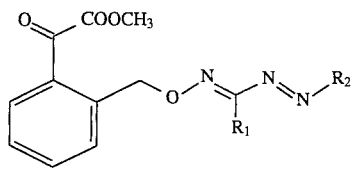

in which $R_1$ and $R_2$ are as defined in claim 1.

22. A phenyl acetate derivative of formula X

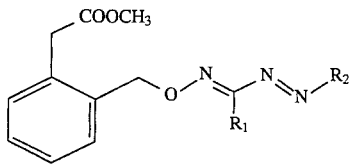

in which $R_1$ and $R_2$ are as defined in claim 1.

* * * * *